(12) United States Patent
Matheny (10) Patent No.: US 10,052,189 B2
(45) Date of Patent: Aug. 21, 2018

(54) REINFORCED VASCULAR PROSTHESES

(71) Applicant: Robert G Matheny, Norcross, GA (US)

(72) Inventor: Robert G Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 983 days.

(21) Appl. No.: 14/337,915

(22) Filed: Jul. 22, 2014

(65) Prior Publication Data

US 2015/0081010 A1    Mar. 19, 2015

Related U.S. Application Data

(63) Continuation of application No. 14/031,520, filed on Sep. 19, 2013, now abandoned, and a continuation-in-part of application No. 14/031,423, filed on Sep. 19, 2013, now abandoned.

(51) Int. Cl.
| | |
|---|---|
| *A61F 2/82* | (2013.01) |
| *A61L 27/36* | (2006.01) |
| *A61F 2/07* | (2013.01) |
| *A61L 27/50* | (2006.01) |
| *A61L 27/54* | (2006.01) |
| *A61L 27/18* | (2006.01) |
| *A61F 2/06* | (2013.01) |

(52) U.S. Cl.
CPC ............. *A61F 2/07* (2013.01); *A61F 2/06* (2013.01); *A61F 2/82* (2013.01); *A61L 27/18* (2013.01); *A61L 27/3629* (2013.01); *A61L 27/3633* (2013.01); *A61L 27/507* (2013.01); *A61L 27/54* (2013.01); *A61F 2210/0004* (2013.01); *A61F 2210/0014* (2013.01); *A61F 2210/0076* (2013.01); *A61F 2220/0075* (2013.01); *A61L 2300/216* (2013.01); *A61L 2300/252* (2013.01); *A61L 2300/40* (2013.01); *A61L 2300/41* (2013.01); *A61L 2300/434* (2013.01); *A61L 2300/64* (2013.01); *A61L 2430/20* (2013.01)

(58) Field of Classification Search
CPC .................. A61F 2/07; A61F 2002/075; A61F 2002/072; A61F 2250/0008; A61F 2/89; A61F 2/90; A61F 2/915; A61F 2210/0076; A61F 2220/0058; A61F 2/06; A61F 2210/0004; A61F 2/82; A61L 27/36; A61L 27/3633; A61L 27/54
See application file for complete search history.

(56) References Cited

U.S. PATENT DOCUMENTS

| | | | | |
|---|---|---|---|---|
| 7,569,233 | B2 * | 8/2009 | Malaviya | A61L 27/3629 264/109 |
| 8,097,272 | B2 * | 1/2012 | Addison | A61F 13/00008 424/443 |
| 8,691,259 | B2 * | 4/2014 | Bowman | A61F 2/0063 424/422 |

(Continued)

*Primary Examiner* — Seema Mathew
(74) *Attorney, Agent, or Firm* — Francis Law Group (57) ABSTRACT

Vascular grafts for treating, reconstructing and replacing damaged or diseased cardiovascular vessels that are formed from decellularized extracellular matrix (ECM). The vascular grafts include structural reinforcement means, such as a strand of wound biodegradable polymeric material disposed proximate the outer surface of the graft.

4 Claims, 2 Drawing Sheets

(56) References Cited

U.S. PATENT DOCUMENTS

| | | | | |
|---|---|---|---|---|
| 8,771,294 B2* | 7/2014 | Sepetka | ............ | A61B 17/12022 606/144 |
| 2003/0130747 A1* | 7/2003 | Abraham | ................. | A61L 27/24 623/23.72 |
| 2004/0093080 A1* | 5/2004 | Helmus | ................. | A61L 27/507 623/2.41 |
| 2005/0187604 A1* | 8/2005 | Eells | .................... | A61L 27/3629 623/1.13 |
| 2006/0116713 A1* | 6/2006 | Sepetka | ............ | A61B 17/12022 606/200 |
| 2006/0136047 A1* | 6/2006 | Obermiller | ................ | A61F 2/06 623/1.41 |
| 2008/0200979 A1* | 8/2008 | Dieck | .................... | A61F 2/0077 623/1.44 |
| 2010/0268321 A1* | 10/2010 | McDermott | .............. | A61F 2/07 623/1.15 |
| 2012/0239161 A1* | 9/2012 | Datta | ...................... | A61L 27/18 623/23.72 |
| 2013/0116799 A1* | 5/2013 | Derwin | ..................... | A61F 2/02 623/23.72 |
| 2016/0022407 A1* | 1/2016 | Matheny | ................... | A61F 2/06 623/1.13 |
| 2016/0106838 A1* | 4/2016 | D'Agostino | ........ | A61B 17/7233 623/23.51 |
| 2016/0374800 A1* | 12/2016 | You | ........................... | A61F 2/18 604/514 |

* cited by examiner

REINFORCED VASCULAR PROSTHESES

CROSS-REFERENCES TO RELATED APPLICATIONS

This application is a continuation-in-part of U.S. application Ser. No. 14/031,520, filed on Sep. 19, 2013, which is a continuation-in-part of U.S. application Ser. No. 14/031,423, filed on Sep. 19, 2013, which claims the benefit of U.S. Application Nos. 61/710,992, filed on Oct. 8, 2012.

FIELD OF THE INVENTION

The present invention relates to methods and apparatus for treating damaged or diseased cardiovascular vessels. More particularly, the present invention relates to reinforced vascular grafts or prostheses for treating and/or reconstructing damaged or diseased cardiovascular vessels.

BACKGROUND OF THE INVENTION

As is well known in the art, various vascular grafts or prostheses are often employed to treat and reconstruct damaged or diseased cardiovascular vessels.

Currently, the vascular grafts often employed to reconstruct (or replace) damaged or diseased cardiovascular vessels are autologous arteries and veins, e.g., internal mammary artery or saphenous vein; particularly, in situations where small diameter (i.e. 3-4 mm) vessels are required, such as below the knee and coronary artery bypass grafting.

Autologous arteries and veins are, however, often unavailable, due to prior harvest, or unsuitable, due to arterial disease.

When autologous arteries and veins are unavailable or unsuitable, synthetic polytatrafluoroethylene (PTFE) or Dacron® grafts are often employed to reconstruct or replace damaged or diseased cardiovascular vessels; particularly, in situations where large diameter (i.e. ≥6 mm) vessels are required.

There are, however, numerous drawbacks and disadvantages associated with synthetic grafts. A major drawback is the poor median patency exhibited by synthetic grafts, due to stenosis, thromboembolization, calcium deposition and infection. Indeed, it has been found that patency is >25%@3 years using synthetic and cryopreserved grafts in peripheral and coronary bypass surgeries, compared to >70% for autologous vascular grafts. See Chard, et al., *Aorta-Coronary Bypass Grafting with Polytetrafluoroehtylene Conduits: Early and Late Outcome in Eight Patients*, j Thorac Cardiovasc Surg, vol. 94, pp. 312-134 (1987).

Decellularized bovine internal jugular xenografts and human allograft vessels from cadavers have also employed to reconstruct or replace damaged or diseased cardiovascular vessels. Such grafts are, however, prone to calcification and thrombosis and, thus, have not gained significant clinical acceptance.

Vascular prostheses constructed of various biodegradable materials, such as poly (trimethylene carbonate), have also been developed to reconstruct damaged or diseased cardiovascular vessels. There are, however, several drawbacks and disadvantages associated with such prostheses.

One major disadvantage is that the biodegradable materials and, hence, prostheses formed therefrom, often break down at a faster rate than is desirable for the application. A further disadvantage is that the materials can, and in many instances will, break down into large, rigid fragments that can cause obstructions in the interior of the vessel.

More recently, vascular grafts comprising various remodelable materials, such as extracellular matrix sheets, have been developed to treat and reconstruct damaged or diseased cardiovascular vessels. Illustrative are the vascular grafts disclosed in Applicant's Co-Pending application Ser. No. 13/573,226.

Although such grafts have garnered overwhelming success and, hence, gained significant clinical acceptance, there are a few drawbacks associated with such grafts. Among the drawbacks are the construction and, hence, configuration of the noted vascular grafts.

As discussed in detail in Co-Pending application Ser. No. 13/573,226, such grafts typically comprise one or more sheets of ECM tissue, e.g., small intestine submucosa, which is secured at one edge to form a tubular structure. The secured edge or seam can, and in many instances will, disrupt blood flow through the graft. A poorly secured edge also poses a significant risk of thrombosis.

Further, in some instances, wherein the ECM graft comprises two or more sheets, i.e. a multi-sheet laminate, such as disclosed in Co-pending application Ser. No. 14/031,423, the laminate structure is prone to delamination.

Thus, readily available, versatile vascular grafts that are not prone to calcification, thrombosis and intimal hyperplasia would fill a substantial and growing clinical need.

It is therefore an object of the present invention to provide vascular grafts (including "endografts") that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.

It is another object of the present invention to provide vascular grafts that can effectively replace or improve biological functions or promote the growth of new tissue in a subject.

It is another object of the present invention to provide vascular grafts that induce host tissue proliferation, bioremodeling and regeneration of new tissue and tissue structures with site-specific structural and functional properties.

It is another object of the present invention to provide vascular grafts that are capable of administering a pharmacological agent to host tissue and, thereby produce a desired biological and/or therapeutic effect.

SUMMARY OF THE INVENTION

The present invention is directed to reinforced vascular grafts or prostheses for treating, reconstructing or replacing damaged or diseased cardiovascular vessels.

As discussed in detail herein, the vascular grafts comprise tubular members having first (or proximal) and second (or distal) ends.

In a preferred embodiment of the invention, the tubular members comprise a decellularized ECM material from a mammalian tissue source, i.e. tubular ECM members.

According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In a preferred embodiment, the mammalian tissue source comprises an adolescent mammalian tissue source.

In some embodiments of the invention, the tubular ECM members and, hence, vascular grafts formed therefrom, further comprise at least one additional biologically active agent or composition, i.e. an agent that induces or modulates a physiological or biological process, or cellular activity, e.g., induces proliferation, and/or growth and/or regeneration of tissue.

In some embodiments, the biologically active agent comprises a cell, such as a human embryonic stem cell, fetal cardiomyocyte, myofibroblast, mesenchymal stem cell, etc.

In some embodiments, the biologically active agent comprises a growth factor, such as a transforming growth factor-alpha (TGF-α), transforming growth factor-beta (TGF-β), fibroblast growth factor-2 (FGF-2), basic fibroblast growth factor (bFGF), and vascular epithelial growth factor (VEGF).

In some embodiments, the tubular ECM members and, hence, vascular grafts formed therefrom, further comprise at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a statin, i.e. a HMG-CoA reductase inhibitor, such as cerivastatin.

In a preferred embodiment of the invention, the tubular ECM members and, hence, vascular grafts formed therefrom, further comprise reinforcement means, i.e. reinforced vascular prostheses.

In some embodiments, the reinforcement means comprises a thin strand or thread of reinforcing material that is wound around the tubular member.

In some embodiments, the reinforcing strand comprises a biocompatible and biodegradable polymeric material.

In some embodiments, the reinforcing strand comprises an ECM strand or thread.

In some embodiments, the reinforcing strand comprises a biocompatible metal, such as stainless steel or Nitinol®, or a biocompatible and biodegradable metal, such as magnesium.

In some embodiments, the reinforcement means comprises a braided or mesh configuration.

In some embodiments of the invention, the tubular ECM members and, hence, vascular grafts formed therefrom, further comprise at least one anchoring mechanism.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "graft" and "endograft" are used interchangeably herein, and mean and include a structure that is configured for implantation in a cardiovascular structure, e.g., a cardiovascular vessel.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The term "Artelon", as used herein, means a poly(urethane urea) material distributed by Artimplant AB in Goteborg, Sweden.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGS), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological agent" and/or "biologically active agent" and/or "pharmacological composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The term "adolescent", as used herein, means and includes a mammal that is preferably less than three (3) years of age.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to vascular grafts or prostheses for treating, reconstructing or replacing damaged or diseased cardiovascular vessels.

In a preferred embodiment of the invention, the tubular members comprise a decellularized ECM material from a mammalian tissue source. As stated above, according to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

In a preferred embodiment, the mammalian tissue source comprises an adolescent mammalian tissue source, i.e. an adolescent mammal, such as a piglet, which is preferably less than three (3) years of age.

In a preferred embodiment, the ECM material is decellularized and, hence, remodelable. According to the invention, the ECM material can be decellularized by various conventional means. In a preferred embodiment, the ECM material is decellularized via one of the unique Novasterilis processes disclosed in U.S. Pat. No. 7,108,832 and U.S. patent application Ser. No. 13/480,204; which are incorporated by reference herein in their entirety.

According to the invention, upon implanting a vascular graft of the invention in a cardiovascular system of a subject, the vascular graft induces host tissue proliferation, bioremodeling, including neovascularization, e.g., vasculogenesis, angiogenesis, and intussusception, and regeneration of tissue structures with site-specific structural and functional properties. The graft also provides a vessel having a smooth, non-thrombogenic interior surface.

As stated above, in some embodiments of the invention, the vascular grafts further comprise at least one additional biologically active agent or composition, i.e. an agent that induces or modulates a physiological or biological process, or cellular activity, e.g., induces proliferation, and/or growth and/or regeneration of tissue.

In a preferred embodiment of the invention, the biologically active agent is similarly derived from an adolescent mammal, i.e. a mammal less than three (3) years of age.

Suitable biologically active agents include any of the aforementioned biologically active agents, including, without limitation, the aforementioned cells and proteins.

In some embodiments of the invention, the biologically active agent comprises a growth factor selected from the group comprising transforming growth factor-alpha (TGF-α), transforming growth factor-beta (TGF-β), fibroblast growth factor-2 (FGF-2), basic fibroblast growth factor (bFGF) and vascular epithelial growth factor (VEGF).

According to the invention, upon implanting a vascular graft of the invention in a cardiovascular system of a subject, the growth factors link to and interact with at least one molecule in the vascular graft and further induce and/or control host tissue proliferation, bioremodeling, and regeneration of new tissue structures.

In some embodiments of the invention, the biologically active agent comprises a protein selected from the group comprising proteoglycans, glycosaminoglycans (GAGs), glycoproteins, heparins, chondroitin sulfate B (dermatan sulfate), chondroitin sulfate A, heparin sulfates, and hyaluronic acids.

In some embodiments of the invention, the protein comprises a cytokine selected from the group comprising a stem cell factor (SCF), stromal cell-derived factor-1 (SDF-1), granulocyte macrophage colony-stimulating factor (GM-CSF), interferon gamma (IFN-gamma), interleukin-3, interleukin-4, interleukin-10, interleukin-13, leukemia inhibitory factor (LIF), amphiregulin, thrombospondin 1, thrombospondin 2, thrombospondin 3, thrombospondin 4, thrombospondin 5, and angiotensin converting enzyme (ACE).

According to the invention, upon implanting a vascular graft of the invention in a cardiovascular system of a subject, the proteins similarly link to and interact with at least one molecule in the graft and further induce and/or control host tissue proliferation, bioremodeling, and regeneration of new tissue structures.

In some embodiments, the vascular grafts further comprise at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, antineoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises one of the aforementioned anti-inflammatories.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. The properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

In some embodiments of the invention, the vascular grafts further comprise at least one outer coating. In some embodiments, the outer coating comprises a pharmacological composition.

In some embodiments of the invention, the vascular grafts further comprise reinforcement means, i.e. reinforced vascular grafts.

As discussed in detail below, in some embodiments, the reinforcement means comprises a thin strand or thread of reinforcing material that is wound around the tubular graft. According to the invention, the reinforcing strand can comprise various biocompatible materials.

In a preferred embodiment, the reinforcing strand comprises a biocompatible and biodegradable polymeric material. According to the invention, suitable biodegradable polymeric materials similarly include, without limitation, polyhydroxyalkonates (PHAs), polylactides (PLLA) and polyglycolides (PLGA) and their copolymers, polyanhydrides, and like polymers.

A further suitable polymeric material comprises "Artelon", i.e. a polyurethane urea) material distributed by Artimplant AB in Goteborg, Sweden.

According to the invention, the reinforcing strand can also comprise an ECM strand or thread, such as a small intestine or urinary bladder submucosa suture.

According to the invention, the reinforcing strand can be disposed on the outer surface of the graft manually or via an electro-spin procedure.

According to the invention, the reinforcing strand can also comprise a biocompatible metal, such as stainless steel or Nitinol®, or a biocompatible and biodegradable metal, such as magnesium.

In some embodiments, the reinforcement means comprises a braided or mesh configuration or other conventional stem structure.

In some embodiments of the invention, the vascular grafts further comprise at least one anchoring mechanism, such as disclosed in Co-pending application Ser. Nos. 13/782,024 and 13/686,131; which are incorporated by reference herein in their entirety.

Figure 1A:
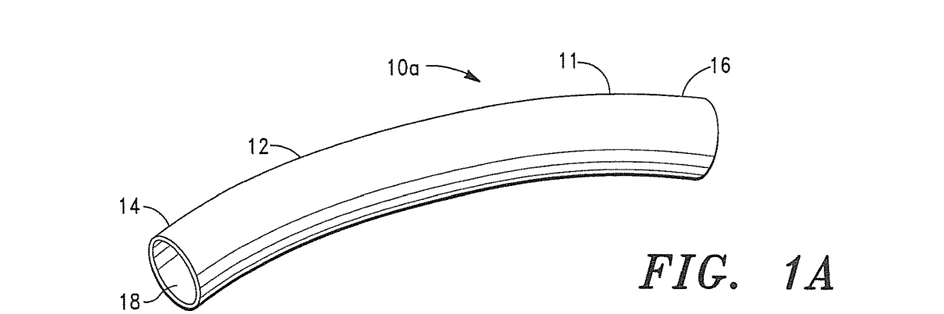
FIG. 1A is a perspective view of one embodiment of a tubular ECM vascular graft, in accordance with the invention.
Figure 1B:
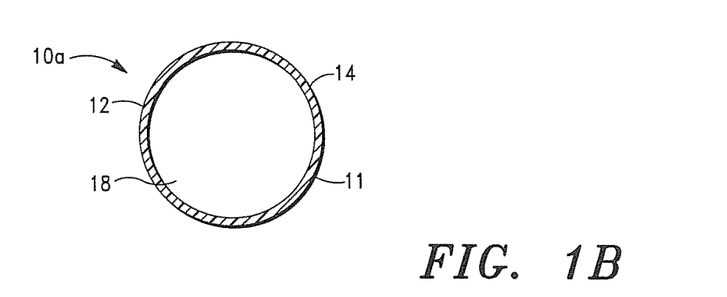
FIG. 1B is a side or edge plan view of the tubular ECM vascular graft shown in FIG. 1A, in accordance with the invention.

Referring now to FIGS. 1A and 1B, there is shown one embodiment of a vascular graft of the invention. As illustrated in FIG. 1A, the graft 10a comprises a continuous tubular member 12 having proximal 14 and distal 16 ends, and a lumen 18 that extends therethrough.

As indicated above, in a preferred embodiment of the invention, the tubular member 12 comprises a decellularized ECM material. As also indicated above, preferably, the ECM material is derived from an adolescent mammal, i.e. a mammal less than three (3) years of age.

According to the invention, the tubular member 12, and, hence vascular graft 10a (and grafts 10b-10d, discussed below) formed therefrom, can have various diameters, e.g. 3.0 mm, 10.0 mm, etc.

In some embodiments of the invention, the vascular graft 10a further comprises at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, growth factors and proteins.

In some embodiments, the vascular graft 10a further comprises at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises a statin, i.e. a HMG-CoA reductase inhibitor.

Figure 2A:
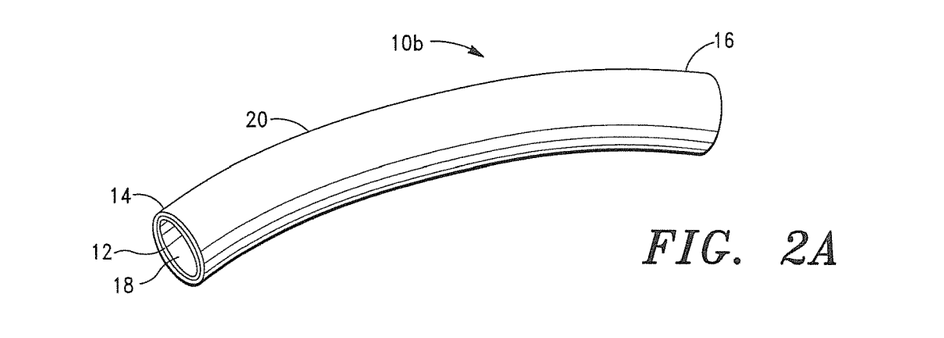
FIG. 2A is a perspective view of one embodiment of a coated ECM vascular graft, in accordance with the invention.
Figure 2B:
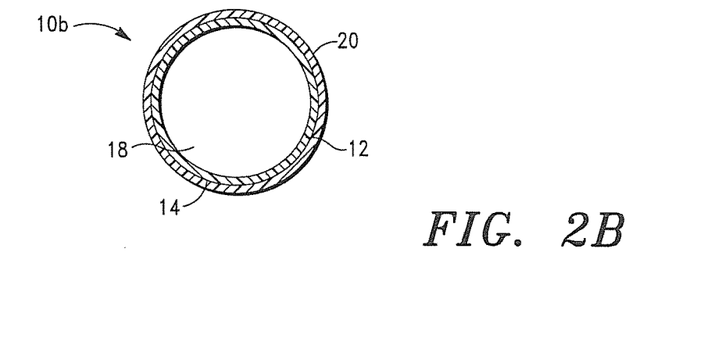
FIG. 2B is a side or edge plan view of the coated ECM vascular graft shown in FIG. 2A, in accordance with the invention.

Referring now to FIGS. 2A and 2B, there is shown another embodiment of a vascular graft of the invention. As illustrated in FIG. 2A, the endograft 10b similarly comprises a continuous tubular member 12 having proximal 14 and distal 16 ends, and a lumen 18 that extends therethrough.

However, in this embodiment, the vascular endograft 10b further comprises at least one outer coating 20. In some embodiments, the outer coating 20 comprises a pharmacological composition.

As indicated above, in some embodiments of the invention, the vascular grafts of the invention further comprise reinforcement means, i.e. reinforced vascular grafts.

Figure 3A:
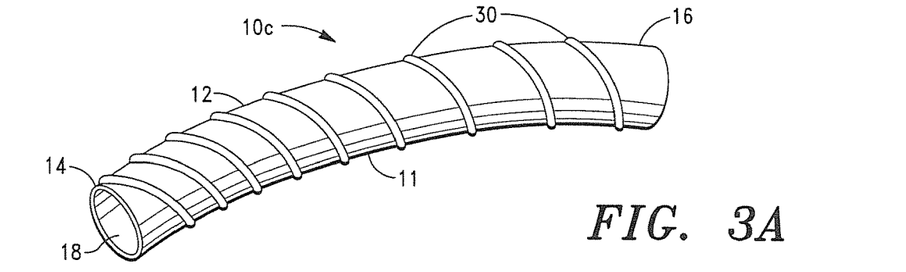
FIG. 3A is a perspective view of one embodiment of a reinforced ECM vascular graft, in accordance with the invention.
Figure 3B:
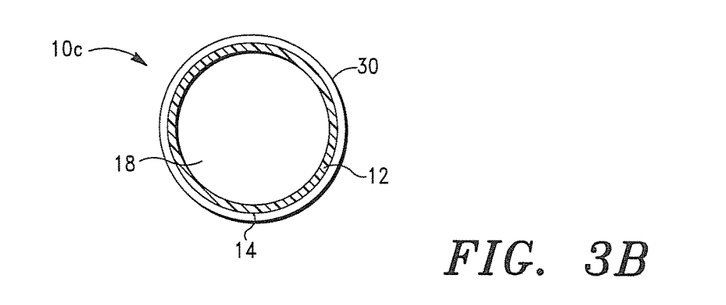
FIG. 3B is a side or edge plan view of the reinforced ECM vascular egraft shown in FIG. 3A, in accordance with the invention.

Referring now to FIGS. 3A and 3B there is shown one embodiment of a reinforced vascular graft of the invention. As illustrated in FIG. 3A, the graft 10c similarly comprises a continuous tubular member 12 having proximal 14 and distal 16 ends, and a lumen 18 that extends therethrough.

The graft 10c further comprises reinforcement means, which, in the illustrated embodiment, comprises a thin strand or thread of reinforcing material 30, which is wound around the tubular endograft 10c, and, hence, disposed proximate the outer surface 11 thereof. According to the invention, the reinforcing strand 30 can comprise various biocompatible materials.

As indicated above, in a preferred embodiment, the reinforcing strand 30 comprises a biocompatible and biodegradable polymeric material. Suitable biodegradable polymeric materials similarly include, without limitation, polyhydroxyalkonates (PHAs), polylactides (PLLA) and polyglycolides (PLEA) and their copolymers, polyanhydrides, and like polymers.

In some embodiments, the reinforcing strand 30 can alternatively comprise an ECM strand or thread, such as a small intestine or urinary bladder submucosa suture. In a preferred embodiment, the ECM strand comprises a cross-linked ECM material.

According to the invention, the reinforcing strand 30 can also comprise a biocompatible metal, such as stainless steel or Nitinol®, or a biocompatible and biodegradable metal, such as magnesium.

As indicated above, in some embodiments, the reinforcement means comprises a braided or mesh configuration.

Figure 4A:
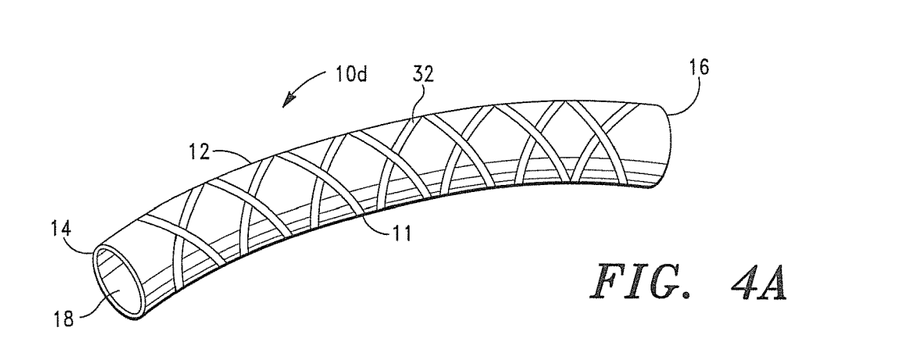
FIG. 4A is a perspective view of another embodiment of a reinforced ECM vascular graft, in accordance with the invention.
Figure 4B:
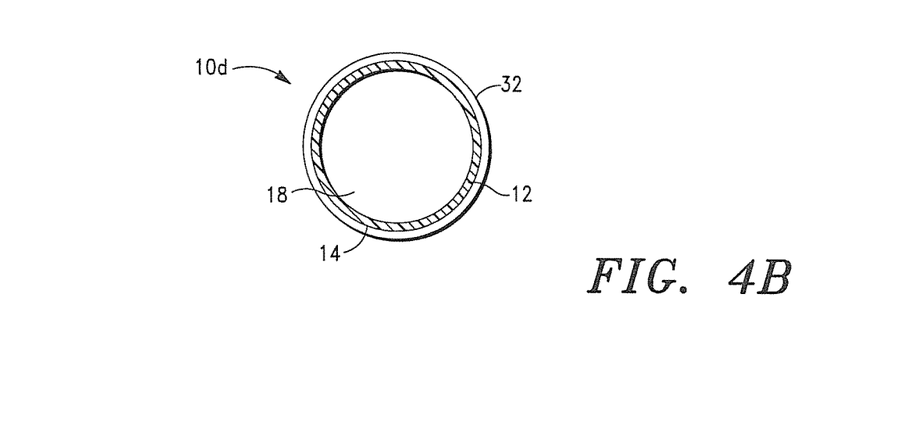
FIG. 4B is a side or edge plan view of the reinforced ECM vascular graft shown in FIG. 4A, in accordance with the invention.

Referring now to FIGS. 4A and 4B there is shown another embodiment of a reinforced vascular graft of the invention (denoted "10d"), wherein the graft 10d includes a braided reinforcing structure 32.

According to the invention, the braided structure 32 can comprise various configurations and can be formed by various conventional means. The braided structure 32 can also comprise any of the aforementioned biocompatible and biodegradable materials.

In a preferred embodiment, the braided structure 32 comprises one of the aforementioned biodegradable polymeric materials.

In some embodiments of the invention, the vascular grafts 10a-10d further comprise at least one anchoring mechanism, such as disclosed in Co-pending application Ser. Nos. 13/782,024 and 13/686,131, which are incorporated by reference herein in their entirety.

As will readily be appreciated by one having ordinary skill in the art, the present invention provides numerous advantages compared to prior art prosthetic valves. Among the advantages are the following:

The provision of reinforced vascular grafts that substantially reduce or eliminate (i) the risk of thrombosis, (ii) intimal hyperplasia after intervention in a vessel, (iii) the harsh biological responses associated with conventional polymeric and metal prostheses, and (iv) the formation of biofilm, inflammation and infection.

The provision of reinforced vascular grafts, which can be effectively employed to treat, reconstruct, replace and improve biological functions or promote the growth of new cardiovascular tissue in a cardiovascular structure.

The provision of reinforced vascular grafts that induce host tissue proliferation, bioremodeling and regeneration of new tissue and tissue structures with site-specific structural and functional properties.

The provision of reinforced vascular grafts, which are capable of administering a pharmacological agent to host tissue and, thereby produce a desired biological and/or therapeutic effect.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A vascular graft for reconstructing damaged cardiovascular vessels, comprising:

a continuous tubular sheet member and a reinforcement member, said tubular member comprising proximal and distal ends, an outer surface region and a lumen that extends therethrough, said tubular sheet member being formed from mammalian tissue in natural sheet form said mammalian tissue comprising decellularized extracellular matrix (ECM) derived from a mammalian tissue source selected from the group consisting of small intestine submucosa (SIS), urinary bladder submucosa (UBS), stomach submucosa (SS), heart tissue, mesothelial tissue and placental tissue, said reinforcement member comprising a continuous, linear strand member that is wound around said tubular sheet member and extends longitudinally from said proximal end of said tubular sheet member to said distal end of said tubular sheet member, wherein a plurality of windings of said linear strand member is disposed proximate said tubular sheet member outer surface, and wherein an exposed outer surface region is disposed between adjoining windings of said plurality of windings, said linear strand member consisting of poly(urethane urea).

2. The vascular graft of claim 1, wherein said tubular sheet member further comprises at least one additional biologically active agent.

3. The vascular graft of claim 2, wherein said biologically active agent comprises a cell selected from the group consisting of a human embryonic stem cell, fetal cardiomyocyte, myofibroblast, and mesenchymal stem cell.

4. The vascular graft of claim 2, wherein said biologically active agent comprises a growth factor selected from the group consisting of a transforming growth factor-alpha (TGF-α), transforming growth factor-beta (TGF-β), basic fibroblast growth factor (bFGF), and vascular epithelial growth factor (VEGF).

* * * * *